(12) United States Patent
Siskin et al.

(10) Patent No.: US 8,204,265 B2
(45) Date of Patent: *Jun. 19, 2012

(54) EAR WARMING ARTICLE INCLUDING ELECTRONIC DEVICE AND EASILY INTERCHANGEABLE ADVERTISING AREAS

(75) Inventors: David R. Siskin, Kentfield, CA (US); Joel A. Schechter, New York, NY (US)

(73) Assignee: David R. Siskin, Kentfield, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/652,323

(22) Filed: Jan. 5, 2010

(65) Prior Publication Data

US 2010/0166243 A1    Jul. 1, 2010

Related U.S. Application Data

(63) Continuation of application No. 10/999,091, filed on Nov. 29, 2004, now Pat. No. 7,668,330, which is a continuation of application No. 10/188,572, filed on Jul. 2, 2002, now Pat. No. 6,888,950.

(51) Int. Cl.
*H04R 1/10* (2006.01)
*H04R 9/06* (2006.01)
*H04R 25/00* (2006.01)

(52) U.S. Cl. .......... 381/334; 381/74; 381/333; 381/376; 381/378; 2/905; 2/906

(58) Field of Classification Search .................. 381/333, 381/334, 301, 74, 376, 378, 72; 2/69, 905, 2/906; 128/864, 867–868
See application file for complete search history.

(56) References Cited

U.S. PATENT DOCUMENTS

| | | |
|---|---|---|
| 2,671,221 A | 3/1954 | Triplett |
| 3,098,121 A | 7/1963 | Wadsworth |
| 4,243,851 A | 1/1981 | Forney |
| (Continued) | | |

FOREIGN PATENT DOCUMENTS

EP    745364 B1    8/2002
(Continued)

OTHER PUBLICATIONS 9 pages from Internet website www.hearmuff.com 2004.

*Primary Examiner* — Vivian Chin
*Assistant Examiner* — Douglas Suthers
(74) *Attorney, Agent, or Firm* — Rimas T. Lukas; Lukas IP Group

(57) ABSTRACT

An ear warming article that can be comprised of a C-shaped resilient band, an outer sleeve and a speaker or other electronic device is described. The outer sleeve is dimensioned to contain the resilient band, and includes two insulating, ear-receiving portions as well as a first opening through which the resilient band can be inserted or removed to yield an assembled or disassembled article, respectively. In a preferred embodiment, the article includes an electronic device having one or more speakers located at the ends of the resilient band; additional openings in the outer sleeve may exist for any control functionality associated with the electronic device(s). The outer sleeve can be comprised of a washable fabric material, particularly suitable as a means for interchangeable advertising (team logo, branding, etc.). In other embodiments, the ear warming article includes additional advertising and/or securing features.

107 Claims, 6 Drawing Sheets

U.S. PATENT DOCUMENTS

| | | | |
|---|---|---|---|
| D258,433 S | 3/1981 | Bulmash | |
| D262,455 S | 12/1981 | Bulmash | |
| D263,043 S | 2/1982 | Petrie | |
| 4,404,434 A | 9/1983 | Pelt | |
| 4,463,223 A | 7/1984 | Yamanoi | |
| 4,499,741 A | 2/1985 | Harris | |
| 4,516,274 A | 5/1985 | Buckland | |
| 4,546,215 A | 10/1985 | Ferraro | |
| D282,020 S | 1/1986 | Gwon | |
| D284,080 S | 6/1986 | Swezey | |
| 4,609,786 A | 9/1986 | Omoto | |
| 4,648,130 A * | 3/1987 | Kuznetz | 455/351 |
| 4,654,898 A | 4/1987 | Ishikawa | |
| 4,669,129 A | 6/1987 | Chance | |
| 4,670,911 A | 6/1987 | Dunford | |
| 4,682,363 A | 7/1987 | Goldfarb | |
| 4,689,822 A | 8/1987 | Houng | |
| 4,727,599 A | 2/1988 | Rappaport | |
| 4,776,042 A | 10/1988 | Hanson | |
| 4,776,044 A | 10/1988 | Makins | |
| 4,791,684 A | 12/1988 | Schwartz | |
| 4,858,248 A * | 8/1989 | Goldsmith et al. | 2/209.13 |
| 4,864,619 A | 9/1989 | Spates | |
| 4,864,646 A | 9/1989 | Nesbit | |
| 4,918,757 A | 4/1990 | Janssen | |
| 4,935,965 A | 6/1990 | Wassell | |
| 4,982,451 A | 1/1991 | Graham | |
| 5,034,995 A | 7/1991 | Ciccone | |
| 5,038,412 A | 8/1991 | Cionni | |
| D322,070 S | 12/1991 | Kitch | |
| 5,117,464 A | 5/1992 | Jones | |
| 5,164,987 A | 11/1992 | Raven | |
| 5,201,856 A | 4/1993 | Edwards | |
| 5,257,420 A | 11/1993 | Byrne, Jr. | |
| 5,327,178 A | 7/1994 | McManigal | |
| 5,329,592 A | 7/1994 | Altman | |
| 5,339,467 A | 8/1994 | Brinkley | |
| 5,395,400 A | 3/1995 | Stafford | |
| 5,420,381 A | 5/1995 | Gardner, Jr. | |
| 5,438,698 A | 8/1995 | Burton | |
| 5,457,751 A | 10/1995 | Such | |
| 5,551,089 A | 9/1996 | Whidden | |
| D375,825 S | 11/1996 | Whidden | |
| 5,617,589 A | 4/1997 | Lacore | |
| 5,625,903 A * | 5/1997 | Schultz et al. | 2/209 |
| 5,632,048 A | 5/1997 | Mortell | |
| 5,680,465 A | 10/1997 | Boyden | |
| D399,206 S | 10/1998 | Yasutomi | |
| 5,835,609 A * | 11/1998 | LeGette et al. | 381/385 |
| 5,881,390 A | 3/1999 | Young | |
| 5,887,286 A | 3/1999 | Waldron | |
| 5,953,434 A | 9/1999 | Boyden | |
| 6,038,329 A | 3/2000 | Lee | |
| 6,069,964 A | 5/2000 | Yang | |
| 6,104,824 A | 8/2000 | Ito | |
| 6,148,446 A | 11/2000 | Leight | |
| 6,195,441 B1 | 2/2001 | Ito | |
| 6,263,085 B1 | 7/2001 | Weffer | |
| D449,591 S | 10/2001 | Arpe | |
| 6,301,367 B1 | 10/2001 | Boyden | |
| 6,319,015 B1 | 11/2001 | Faunce | |
| 6,332,223 B1 | 12/2001 | Le Gette | |
| 6,499,146 B2 | 12/2002 | Bavetta | |
| 6,502,247 B2 | 1/2003 | Le Gette | |
| 6,502,248 B2 | 1/2003 | LeGette | |
| 6,819,772 B2 | 11/2004 | Amae | |
| 2002/0026661 A1 | 3/2002 | LeGette | |

FOREIGN PATENT DOCUMENTS

| | | | |
|---|---|---|---|
| WO | 0176402 A1 | 10/2001 | |

* cited by examiner

EAR WARMING ARTICLE INCLUDING ELECTRONIC DEVICE AND EASILY INTERCHANGEABLE ADVERTISING AREAS

CROSS-REFERENCE TO RELATED APPLICATION

This application is a continuation of U.S. application Ser. No. 10/999,091 filed Nov. 29, 2004 entitled "Ear warming article including electronic device and easily interchangeable advertising areas" which is a continuation of U.S. application Ser. No. 10/188,572 filed Jul. 2, 2002 entitled "Ear warming article including electronic device and easily interchangeable advertising areas" now U.S. Pat. No. 6,888,950 by David R. Siskin and Joel A. Schechter, the entire contents of all the above applications are hereby incorporated herein by reference in their entirety as if fully set forth herein.

FIELD OF THE INVENTION

The present invention relates generally to a warming article for a wearer's head that can include electronic equipment (e.g., earphones, headset, audio- or other data-receiving equipment, etc.), and more specifically to an ear warming article including an audio device that has a novel two-piece construction including easily interchangeable advertising means.

BACKGROUND OF THE INVENTION

There are many prior articles designed to cover portions of an individual's head for warmth and/or protection from the elements, such as hats, headbands, and articles that cover primarily the ears alone. A most common variety of this last type of ear warming, frequently referred to as an "earmuff," is comprised of a resilient, C-shaped band that is worn around the top of an individual's head and ear-receiving portions or pockets located at the ends of the C-shaped band. This arrangement is particularly useful in situations where an individual does not wish to constrain their hair as well as in other situations where additional material might be too bulky or interfere with the user. Furthermore, in many situations where an individual would desire to wear such ear protection and display additional insignia/advertising, a variety of additional functionality can be particularly advantageous.

First, it may be desired to design the earmuff so that it may be positioned or worn around the back of an individual's head. A neck-engaging variety of this design can possess the additional advantage of providing protection and added warmth to a wearer's neck as well. In any arrangement where the C-shaped band traverses the backside of the wearer's head, however, the features and functionality of the remainder of the ear warming article need to accommodate this unconventional positioning. For example, the shape of the ear-engaging portions need to take into account the way the ear warming article is worn.

Second, present ear warming articles do not allow the wearer to listen to music or other audio input by means of an integrated electronic device. At football games and other outdoor events, it is often desirable to have warm ears and listen to the radio or music at the same time. It is a significant drawback of current ear warming articles that they possess little or no ability to work with audio-related devices such as earphones, stereo/radio headphones, receivers (radio, XFM, etc.), audio output devices (CD players, MP3 players, etc.), and other audio or audiovisual electronic devices. Consumers are generally forced to pick between wearing either an ear warming article or radio headphones, or to switch between the two as needed, which is particularly undesirable in poor weather. At best, some products offer earphones as an add-on or accessory to a conventional ear-muff. For individuals who desire to receive the benefit of both ear warming articles and audio-related devices in an integrated device, there is a lack of acceptable articles that satisfy both functions at the same time.

Further, many current ear warming articles are unsatisfactory due to a number of shortcomings related to either their appearance or their capabilities. For example, it is often desirable for such headgear to provide advertising or branding opportunities that are attractive to the wearer and are also economical to produce. Articles of this type are frequently purchased based upon the article's possession of a logo or other insignia that indicates association with an interest (favorite sporting team, company, etc.) of the wearer. The specific detail (size, shape, functionality, attractiveness, etc.) of this insignia can be of utmost importance and can easily form the basis for purchase of the article, particularly when a premium article is desired. Current articles sometimes attempt to provide insignia, however such insignia is frequently unacceptable to the wearer because of the logo's size or location, or even because the logo itself cannot be removed, changed or washed.

Another drawback is that current ear warming articles are typically have a complicated, many-piece construction, frequently making the article difficult to manufacture. Such an approach also often leads to an unwanted appearance and can miss a main objective, such as making a reasonably-priced article that is both comfortable and good-looking while providing protection from inclement weather conditions.

Therefore, current ear-warming articles are generally unable to offer the construction, usefulness, appearance and flexibility required to adequately and cost-effectively provide the functionality desired by today's sophisticated, demanding customers.

SUMMARY OF THE INVENTION

An ear warming article comprising a C-shaped resilient band, an outer sleeve and (in some embodiments) a speaker or other electronic device is described. The outer sleeve is dimensioned to contain the resilient band, and includes two insulating, ear-receiving portions as well as a first opening through which the resilient band can be inserted and removed to yield an assembled or disassembled article, respectively. In a preferred embodiment, the article includes an electronic device having one or more speakers located at the ends of the resilient band; additional openings in the outer sleeve may exist for any control functionality associated with the electronic device(s). The outer sleeve can be comprised of a washable fabric material, particularly suitable as a means for interchangeable advertising (team logo, branding, etc.). In some embodiments, the ear warming article provides coverage and warming benefit to the wearer's neck as well. In additional embodiments, the ear warming article includes additional advertising and/or securing features.

Other features and advantages of the present invention will be apparent from the accompanying drawings and from the detailed description that follows.

DESCRIPTION OF THE INVENTION

A warming article for a wearer's head comprising a C-shaped resilient band, an outer sleeve and (in some embodiments) a speaker or other electronic device is disclosed. Although generally referred to as an ear warming article throughout the specification, it should be understood that the article can also, in some embodiments, provide protection and warmth to the wearer's neck as well. In the following description, for purposes of explanation, numerous specific details are set forth in order to provide an understanding of the present invention. It will be evident, however, to those of ordinary skill in the art that the present invention may be practiced without the specific details. In other instances, well-known structures and devices are shown in block diagram form to facilitate explanation. The description of the preferred embodiments is not intended to limit the scope of the claims appended hereto.

Figure 1:
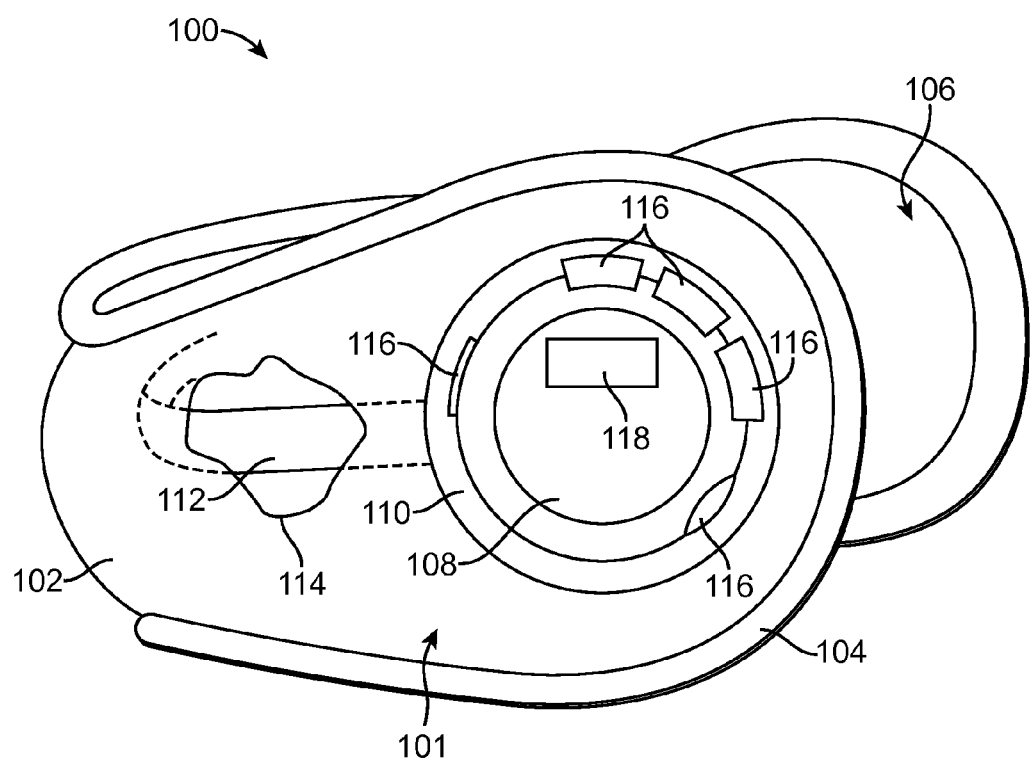
FIG. 1 illustrates an overall three-dimensional perspective side view of an ear warming article, according to one embodiment of the present invention.

An overall three-dimensional side view of an ear warming article, according to one embodiment of the present invention, is illustrated in FIG. 1. As shown in this embodiment, the visible portions of an assembled ear warming article 100 include a soft outer earmuff or "outer sleeve" 101 (made up of a soft outer portion 102, edge material 104 forming a border around the soft outer portion 102, and inner lining material 106 on surfaces that contact the wearer), at least one opening 110, and at least one control portion 108 that protrudes/extends from the soft outer portion 102 through the opening 110 (such as the circular grommet hole depicted in FIG. 1). As shown in the figure, a portion of an inner, resilient band 112 is seen visible through a viewing window 114, exposed only for the sake of illustration, that is located in the soft outer portion 102. The resilient band 112 is a generally C-shaped resilient member that takes the form of a band in this embodiment, although it can assume any shape (e.g., cross-section) that achieves the desired effect of partially encircling the wearer's head.

As will be described in greater detail below in connection with FIG. 6, the control portion 108 of the ear warming article can include display and functional features of electronic components contained within the ear warming article 100. The embodiment of FIG. 1 illustrates several control mechanisms 116 as well as an exemplary display 118 (such as a LCD read-out, or other known screen). The aspects, features and functionality accomplished by these control mechanisms 116 and this display 118 can vary for a variety of desired articles, and thus are referred to here in only a broader sense. Also, it is noted here that the one or more control portions 108, with which these elements (control mechanisms 116 and display 118) are associated, are attached to the resilient band 112, and together the resilient band and the at least one control portion 108 are sometimes referred to as the band/electronic device. That these two elements are sometimes referred to as being grouped together is done for convenience sake only, as the non-sleeve components of the invention can either include or not include an electronic device; indeed, certain embodiments further allow for interchangeable and/or removable electronic devices. In this regard, the fact that some embodiments of the present invention allow for such interchangeability/removability represents another significant feature of those embodiments of the present invention.

With respect to the materials that comprise the ear warming article, the composition of the outer sleeve 101 structure of the presently preferred embodiment is first described. As stated above, the outer sleeve 101 is comprised of a soft outer portion 102, edge material 104 and inner lining material 106, according to the embodiment illustrated in FIG. 1. The soft outer portion 102 can consist of a weather resistant, waterproof and/or breathable material such as, for example, a fabric like nylon or a breathable synthetic fabric like Goretex® (a trademark of W. L. Gore & Associates, Inc.). The edge material 104 can consist of a soft, stretchable material such as Lycra® or a Lycra® blend (trademark of E. I. du Pont and Co.). Internal padding (not shown) that better prevents rubbing or chafing between resilient band and the wearer and that provides a more comfortable article can also be included in the design; such padding can be comprised of any of the various, known open cell foam materials. Finally, the inner lining material 106 can consist of any number of suitable soft, flesh-accommodating fabric material, such as Polarfleece® (a trademark of ADS Corporation) or other soft micro-fleece material.

The composition of the inner components (the resilient band and electronic device), according to one or more embodiments of the present invention, are now generally described. According to one preferred embodiment, the resilient band 112 itself is comprised of a band of resilient, lightweight metal, with the band possessing a spring bias that urges the ear-contacting portions to a position that is slightly narrower than the size of the relevant head; in other words, different sized ear warming articles (such as small, medium and large) would have different neutral positions (the positions at which the spring forces attempt to bias the resilient bands), as well as different curvatures of the bands themselves. In the most preferred embodiment, the resilient metal material is comprised of lightweight spring steel.

In an alternate embodiment, the ear warming article can include different-size inserts and/or inflatable portions that can be interchanged or inflated/deflated, respectively, to change the fit of the ear warming article in order to accommodate the specific size and shape of the wearer's head. These inserts/inflatable portions can be located or associated with either the outer sleeve materials or the resilient band, or they can be entirely independent.

Next, the preferred embodiment comprising an internal AM/FM radio device with embedded AM antenna is described, although the other various embodiments of electronic devices are set forth in more detail after the discussion of radio controls associated with FIG. 6 below. In this preferred embodiment, the internal AM/FM radio device can be located on one or both of the control portions 108 attached to the resilient band 112. As described in more detail in connection with FIG. 6, the controls 116 for the radio device can include volume, analog or digital tuning, user presets (such as input/output or radio station presets), and an OFF/AM/FM three-position switch. Additionally, the display 118 could be a digital station readout, and the power can be supplied by a battery (such as type AAA or AAAA) located in either or both control portions. An auxiliary input jack (for use with an MP3 player, CD player, etc.) can also be located on the ear warming article. Finally, the electronic device of such receiver- or radio-including embodiments can include an embedded antenna that is streamlined within the ear warming article in such a way as to not interfere with the functional and branding features of the inventive article. In the preferred embodiment, the embedded antenna is an AM and/or FM antenna that does not extend beyond the ear warming article.

Figure 2:
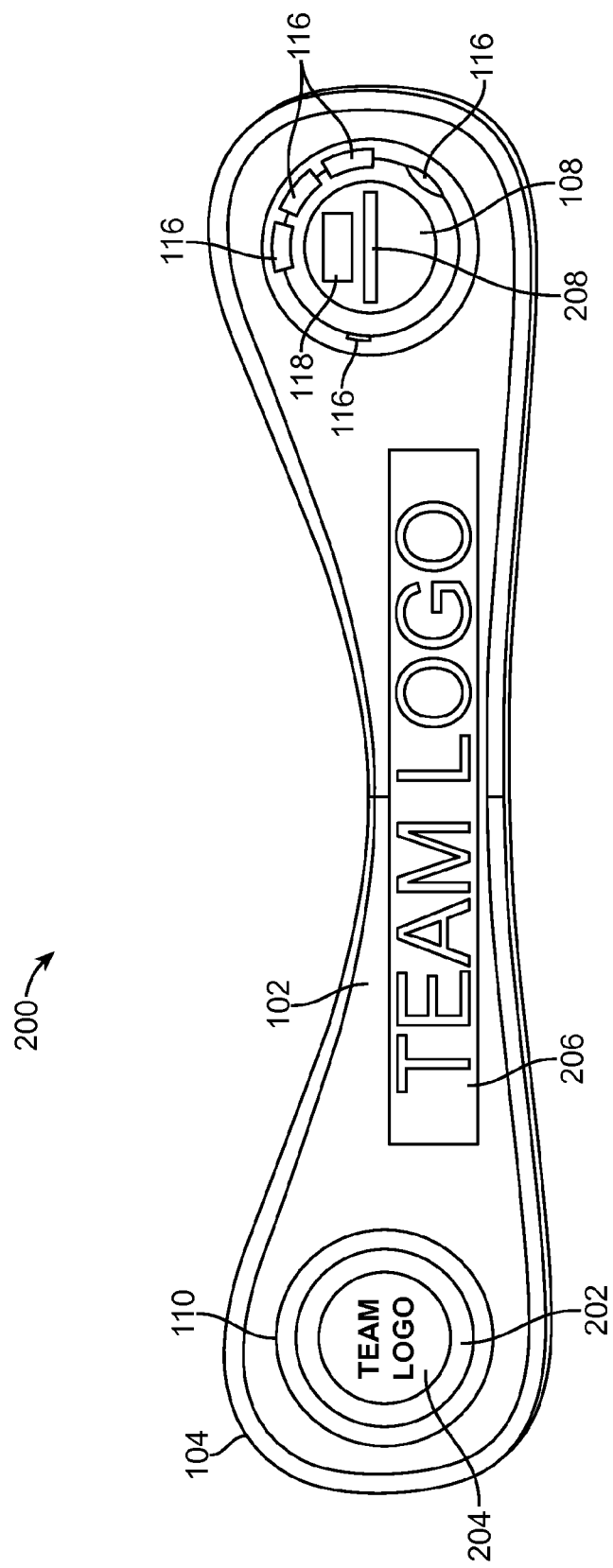
FIG. 2 illustrates a planform view of the outside surface of an ear warming article, according to one embodiment of the present invention.

A planform view of the outside surface of an ear warming article, according to one embodiment of the present invention, is illustrated in FIG. 2. The ear warming article of FIG. 2 is shown laid (or flattened) out, such that it discloses the ear warming article's appearance as if it were not in its customary arcuate or "C" shape. According to the embodiment of FIG. 2, a laid out, outside view 200 of an ear warming article is shown. The laid out, outside view 200 is comprised of the soft outer portion 102 containing a main branding zone 206, the bead of edge material 104 surrounding the soft outer portion 102, and the at least one opening 110 that allows for the protrusion of either a branding portion 202 or a control portion 108 therethrough. The branding portion 202 further includes a branding location 204 that can take the form of a cap or piece of material, preferably hard plastic, that is interchangeably mounted onto or into the branding portion 202. For example, the branding location 204 might constitute a plastic cap having small extension tabs that extend and snap into the branding portion 202 to secure a branding or advertising piece onto the ear warming article. Similarly, the control portion 108 can include an advertising patch 208 in addition to the various controls 116 and/or displays 118 that are located thereon. This advertising patch 208 can be secured or connectable to the control portion 108 by any of the means that the branding location 204 is connected to the branding portion 202, such as Velcro® (a trademark of Velcro Industries B.V.) adhesive, other known physical securement mechanisms (the above-mentioned tabs, etc.), or it may be permanently attached.

In the embodiment of FIG. 2, the main branding zone 206 is located on the outer surface of the soft outer portion 102. This main branding zone 206 can be permanently attached thereto, such that the branding may be changed by using different outer sleeves 101 fitted over the internal resilient band/electronic device structure, or the main branding zone 206 can be removably attached to the soft outer portion 102. In the latter case, the main branding zone 206 can then be removed for such purposes as washing the outer sleeve or when no branding is wanted, and it can then also be easily interchanged when different branding is desired, e.g. replacing a favorite football team logo with a favorite ice hockey team logo.

Figure 3:
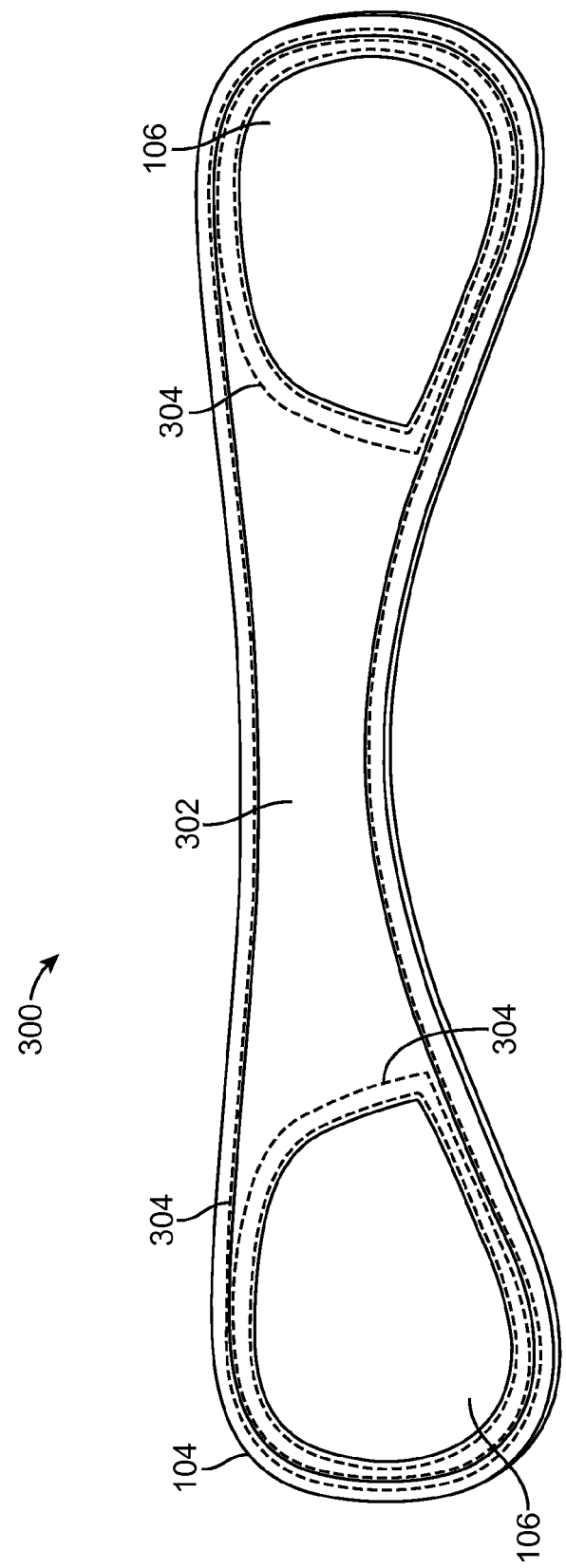
FIG. 3 illustrates a planform view of the inside surface of an ear warming article, according to one embodiment of the present invention.

A planform view of the inside surface of an ear warming article, according to one embodiment of the present invention, is illustrated in FIG. 3. The ear warming article of FIG. 3 is shown laid (or flattened) out, such that it discloses the ear warming article's appearance as if it were not in its customary arcuate or "C" shape. According to the embodiment of FIG. 3, a laid out, inside view 300 of an ear warming article is shown. The laid out, inside view 300 is comprised of the bead of edge material 104, an inside surface 302, and two patches of the inner lining material 106. Stitching 304 is also shown in this figure to illustrate how the some of the exterior pieces of the ear warming article are attached together according to this embodiment. As seen in the embodiment of FIG. 3, the inner lining material 106 (preferably synthetic fleece or microfleece) is present in a shape that corresponds to the shape of the wearer's ears.

Figure 4:
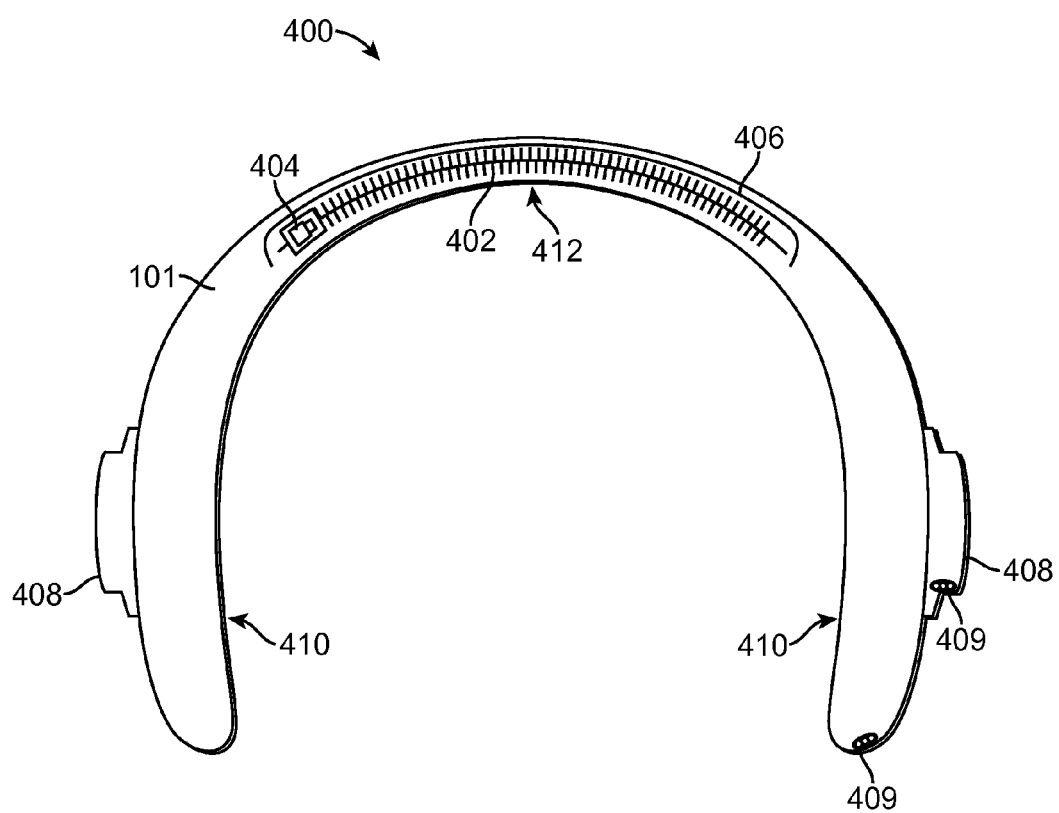
FIG. 4 illustrates a bottom plan view of an ear warming article, according to one embodiment of the present invention.

A bottom plan view of an ear warming article, according to one embodiment of the present invention, is illustrated in FIG. 4. The bottom view 400 of an exemplary ear warming device is shown, illustrating an embodiment wherein a zippable closure 402, which is used for inserting and removing the resilient band and/or electronic devices, is discretely located on a bottom side of the outer sleeve 101. It should be noted that the novelty of the disclosed embodiments of the ear warming article is not necessarily circumscribed by the precise type of closure set forth herein (indeed, some embodiments of the invention, such as those having a permanent outer sleeve, would require no closure), although the novelty of some embodiments can be. Also illustrated in association with the outer sleeve 101 of FIG. 4, are protruding portions 408 (such as control portions 108 or branding portions 202, as seen in FIG. 2), a zipping closure element 404, and a fabric flap 406. In the presently preferred embodiment, the zipper (consisting of the zippable closure 402 and the zipping closure element 404) is located in a slightly recessed fashion within the outer sleeve 101, and the fabric flap 406 is of complementary size so to fit over and hide the zipper. Furthermore, the fabric flap 406 is constructed of the same material as the fabric sleeve and is biased to remain over the zipper (although it can be pushed aside when the user wishes to access the zipper), providing for hidden closure structure that does not affect the appearance of the ear warming article while it is worn.

Additional portions of the ear warming article are indicated in the embodiment of FIG. 4 to assist full comprehension and description of the invention. First, end portions 410 are indicated to point out two regions of the outer sleeve 101 that contact the ears of the wearer, receive the electronics located at the ends of the resilient band, and have other importance. Similarly, the two end portions 410 are connected by means of the connecting portion 412. Finally, two alternate locations for the auxiliary input jack 409 are illustrated in the embodiment of FIG. 4.

Figure 5:
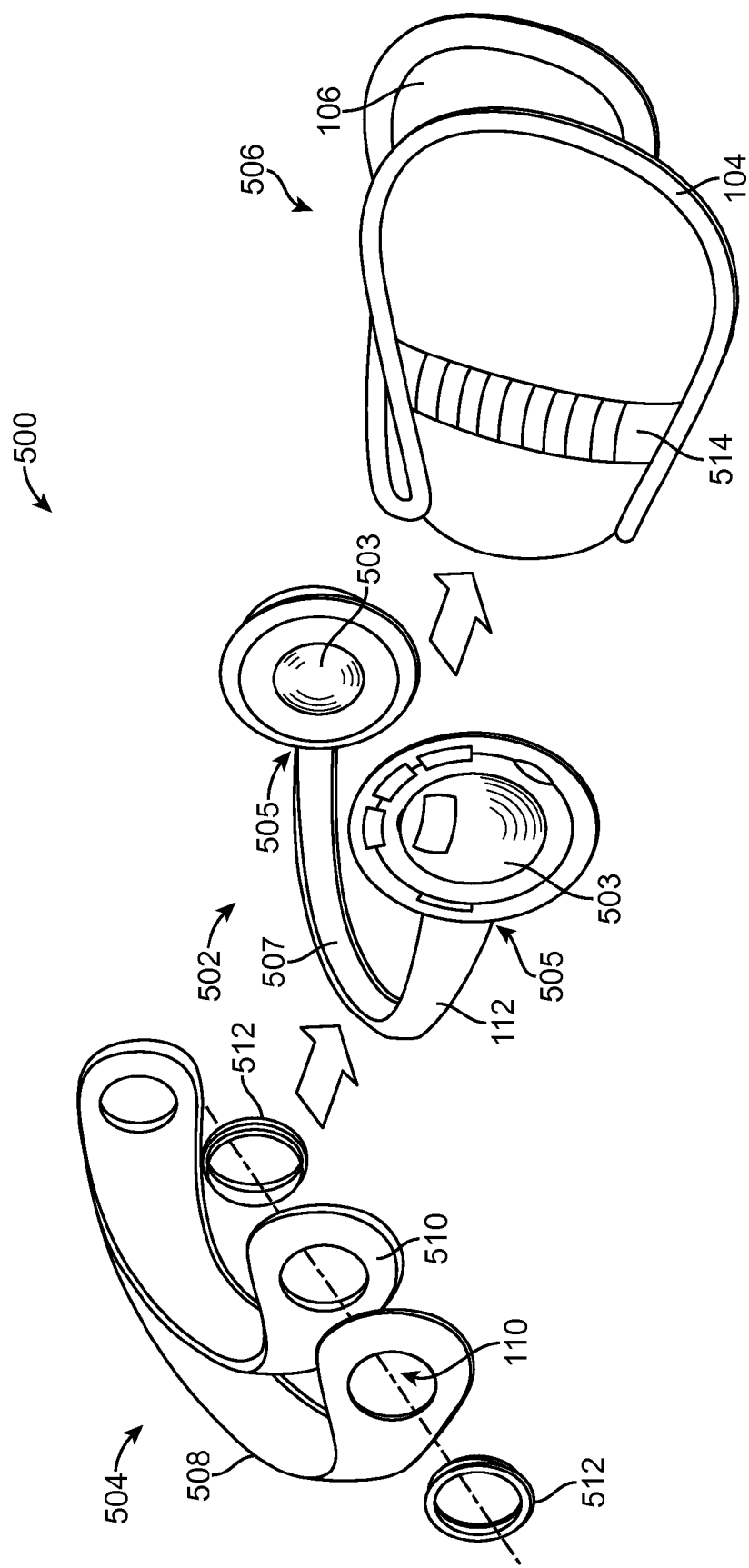
FIG. 5 illustrates an exploded perspective view of an ear warming article, according to a preferred embodiment of the present invention.

An exploded, perspective view of a particular construction of an ear warming article, according to a preferred embodiment of the present invention, is illustrated in FIG. 5. The exploded view 500 illustrated in the embodiment of FIG. 5 consists of a band/electronics portion 502 sandwiched between an exterior foam/fabric portion 504 and an interior foam/fabric portion 506 that together comprise an outer sleeve-like structure 102 that encompasses the band/electronics portion 502. In a preferred embodiment, the exterior foam/fabric portion 504 and the interior foam/fabric portion 506 are of unitary construction (where the band/electronics portion 502 is inserted through the zippable closure 402 as shown in connection with FIG. 4), although the outer sleeve can of course take the form of any multi-part/disassembleable construction. Next, we turn to the novel construction of both this band/electronics portion 502 as well as the outer sleeve-like structure.

The band/electronics portion 502 forms a center, removable portion of this assembly, according to the illustrated embodiment. The preferred electronic devices 503 (e.g., radio, speaker, etc.) incorporated into the ear warming article are generally connected to the distal portions 505 of the central curved portion 507 of the resilient band 112. While these preferred devices have been set forth in more detail below, it is further noted here that all known, portable electronic devices can be incorporated into the ear warming article, provided as add-on or supplemental structure, or both. Similarly, the preferred composition of the resilient band 112 has been detailed above, although certain additional features of it's curvature and resiliency are set forth below.

With respect to the exterior foam/fabric portion 504 of the preferred embodiment illustrated in FIG. 5, it is comprised of an outer nylon layer 508, an open cell foam layer 510, and two 2-part snap grommets 512 (although only one grommet set is illustrated). As mentioned above, this exterior foam/fabric portion 504 can be integral with the interior foam/fabric portion 506 so as to form a unitary piece, or it may fit into (or otherwise snap or be removably secured to) the interior foam/fabric portion 506. The grommet structure defines the opening 110, as discussed in association with FIGS. 1, 2 and 6, through which either the control portion or the branding portions can protrude.

With respect to the interior foam/fabric portion 506 of the preferred embodiment illustrated in FIG. 5, it is comprised of a foam base 512 covered in stretch fabric, an elastic headphone harness 514 (if necessary), and ear-engaging fabric 106 such as soft synthetic fleece or micro-fleece. The foam base 512 has a curved shape that matches and conforms to the head of the wearer, and is characterized by an outer foam skeleton and optionally foam ribs to provide the basic shape, while possessing various channels and cavities to accept the resilient band 112 and any electronic device(s) that are included. Attached between opposed foam ribs are a pair of elastic headphone harnesses 514 to secure any associated headphone, earphone, wires or other, similar supplemental electronic device or its component. Finally, the ear-engaging fabric 106 may be any of the varieties of soft fabric addressed above in connection with FIG. 2.

In a preferred embodiment, the ear warming article can include any type of receiver, such as AM, FM, AM/FM, XM, or a receiver associated with any sort of wire-using or wireless transmitting or broadcasting device, etc. As mentioned above, it is desired to locate the radio and its controls in such a way as to allow straightforward control while maintaining an article of simple and easy construction. Such advantageous location of radio control features and functionality is more fully developed in connection with FIG. 6.

Figure 6:
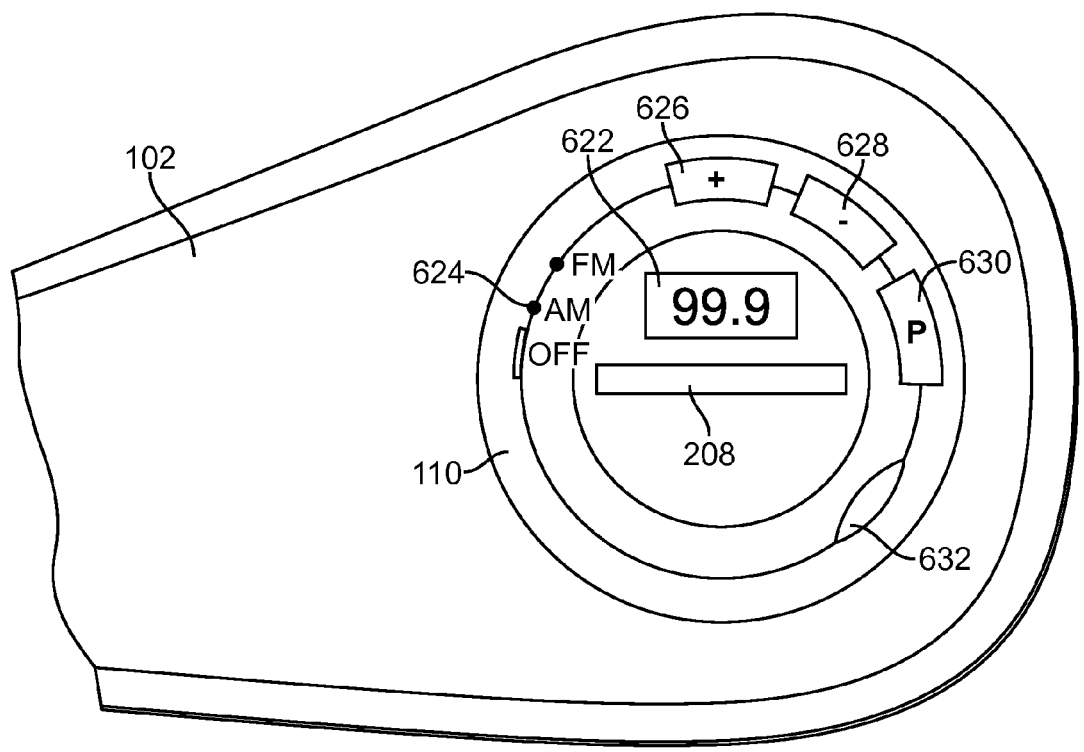
FIG. 6 illustrates an enlarged right side view of a portion of an ear warming article, according to one embodiment of the present invention.

FIG. 6 consists of an enlarged, right plan view of one ear covering portion of a preferred embodiment, illustrating the control portion of an AM/FM radio receiver that extends through one opening 110 of at least one end of the soft outer portion 102. As shown in the embodiment of FIG. 6, the control portion 108 of the receiver extends through an opening 110, which is differentiated from the soft outer portion 102 by means of the grommet 512 or other border material. The control portion 108, then, includes a digital read-out 622 (i.e., the display 118), an OFF/AM/FM switch 624, a channel/station UP button 626, a channel/station DOWN button 628, a 'presets' button 630, a volume control 632, and a advertising patch 208.

As evident from the embodiment of FIG. 6, the functionality of the controls located on the control portion 108 are straightforward, although all controls reasonably related to audio or audiovisual devices are envisioned. In particular, these controls can be any of the controls associated with all known portable audio, video or audio/visual devices such as any of the existing Walkman® or other similar Sony® products, any of the controls used to control any other known devices possessing such potential audio-output (e.g., TV production equipment, any recording equipment, surveillance equipment, etc.), any of the controls used to modify audio data such as may be found in graphic equalizer equipment (tuners, etc.), and/or other controls found on electronic devices that can be carried on or with a wearer. For purposes of illustrating one such exemplary device, the following details of one specific embodiment of the invention are set forth: the digital read-out 622 functions to display such things as the currently selected radio station, the particular preset, the type of broadcast (AM or FM), the volume level and/or other relevant parameters (in another embodiment, the digital read-out 622 can be located underneath a branded lens); the OFF/AM/FM switch 624 turns the radio on, tuned to either frequency modulated (FM) or amplitude modulated (AM) receiving mode; the channel station UP button 626 and DOWN button 628 are used to change the radio, station and/or to effectuate related seek and scan functionality; the 'presets' button 630 is used to toggle the receiver through a variety of previously-established radio stations; and the volume control 632 provides either digital or analog control of speaker volume. However, it is noted again that a variety of other electronic devices are also contemplated with the present invention.

In the foregoing, an ear warming article having an optional electronic device has been described. Although the present invention has been described with reference to specific exemplary embodiments, it will be evident that various modifications and changes may be made to these embodiments without departing from the broader spirit.

What is claimed is:

1. An article for the ears comprising:
   earmuffs having two insulating ear portions; each ear portion located at the ends of a band; and
   at least one speaker located in at least one of the ear portions;
   the article further including at least one sleeve;
   wherein the sleeve or at least a portion of the sleeve is interchangeable or removable.

2. The article of claim 1 wherein the sleeve encompasses the band.

3. The article of claim 1 wherein the sleeve encloses the two insulating ear portions.

4. The article of claim 1
   wherein an electronic wire is concealed within a sleeve.

5. The article of claim 1 further including an opening located in the sleeve through which the at least one speaker can be inserted and removed.

6. The article of claim 1 wherein the sleeve includes a first opening in the sleeve at the location of one of the ear portions.

7. The article of claim 6 wherein the sleeve includes a second opening in the sleeve at the location of the other ear portion.

8. The article of claim 1 further comprising:
   an electronics portion including the at least one speaker sandwiched between an exterior fabric portion and an interior fabric portion that together comprise the sleeve that encompasses the electronics portion, band and ear portions.

9. The article of claim 8 further including the band portion located between the exterior fabric portion and interior fabric portion.

10. The article of claim 8 comprising at least one padding portion located between the interior fabric portion and the electronics portion.

11. The article of claim 8 wherein the electronics portion includes the at least one speaker connectable to an electronic device.

12. The article of claim 1 further including two speakers; one speaker being located at one ear portion and the other speaker being located at the other ear portion.

13. The article of claim 8 wherein the electronics portion further includes at least one electronic device connected to the at least one speaker.

14. The article of claim 8 wherein the electronics portion includes an electronic device for producing an audio output in the at least one speaker; the electronic device including a receiver associated with a wire-using or wireless transmitting or broadcasting device.

15. The article of claim 1 further including at least one harness configured to secure any associated headphone, earphone, speaker, wires or other electronic device or its component inside the sleeve.

16. The article of claim 15 wherein the harness is elastic.

17. The article of claim 1 wherein the sleeve includes a zipping closure element for inserting and removing the earmuffs.

18. The article of claim 17 wherein the sleeve includes a fabric flap configured to hide the zipping closure element.

19. The article of claim 1 further including at least one opening in the sleeve and a control portion extending through the opening.

20. The article of claim 1 further including a radio device connected to the at least one speaker.

21. The article of claim 1 further including a receiver associated with a wireless electronic transmitting or broadcasting device.

22. The article of claim 1 further including an opening in the sleeve configured for inserting and removing an electronic device.

23. The article of claim 1 further including an input jack for connecting the at least one speaker to an external electronic device.

24. An article for the ears comprising:
earmuffs having two insulating ear portions; each ear portion located at the ends of a band; and
at least one speaker located in at least one of the ear portions;
wherein at least one of the ear portions is interchangeable or removable.

25. The article of claim 24 wherein the ear portions consist of soft, flesh-accommodating and insulating material configured to provide comfort in cold weather.

26. The article of claim 24 wherein the ear portions include an outer portion, an inner portion and edge material forming a border around at least a portion of the outer portion and inner portion.

27. The article of claim 24 further including a radio device connected to the at least one speaker.

28. The article of claim 24 further including a receiver associated with a wireless electronic transmitting or broadcasting device.

29. The article of claim 24 further including an interchangeable or removable electronic device.

30. The article of claim 24 wherein the band supports the article on the ears.

31. The article of claim 24
wherein an electronic wire is concealed within the band.

32. The article of claim 24 wherein at least one of the ear portions includes an opening adapted to expose a control portion to provide access to one or more control mechanisms.

33. The article of claim 24 wherein at least one of the ear portions includes an opening configured for inserting and removing an electronic device.

34. The article of claim 24 further including two speakers; one speaker being located at one ear portion and the other speaker being located at the other ear portion.

35. The article of claim 24 further including an electronic device for producing an audio output in the at least one speaker; the electronic device including a receiver associated with a wire-using or wireless transmitting or broadcasting device.

36. The article of claim 24 further including an input jack for connecting the at least one speaker to an external electronic device.

37. The article of claim 24 further including a sleeve encompassing the earmuffs.

38. The article of claim 24 further including an opening at the location of one of the ear portions.

39. An article for the ears comprising:
earmuffs having two insulating ear portions; each ear portion located at the ends of a band;
at least one speaker located in at least one of the ear portions; and
at least one sleeve;
wherein the sleeve or at least a portion of the sleeve is a removable branding portion.

40. The article of claim 39 wherein the sleeve encompasses the band.

41. The article of claim 39 wherein the sleeve encloses the two insulating ear portions.

42. The article of claim 39 wherein an electronic wire is concealed within the sleeve.

43. The article of claim 39 further including an opening located in the sleeve along the length of the band through which the at least one speaker can be inserted and removed.

44. The article of claim 39 further including an opening located in the sleeve through which the at least one speaker can be inserted and removed.

45. The article of claim 39 wherein the sleeve includes a first opening in the sleeve at the location of one of the ear portions.

46. The article of claim 45 wherein the sleeve includes a second opening in the sleeve at the location of the other ear portion.

47. The article of claim 39 further comprising:
an electronics portion including the at least one speaker sandwiched between an exterior fabric portion and an interior fabric portion that together comprise the sleeve that encompasses the electronics portion, band and ear portions.

48. The article of claim 47 further including at least one padding portion located between the interior fabric portion and the electronics portion.

49. The article of claim 47 wherein the electronics portion further includes at least one electronic device connected to the at least one speaker.

50. The article of claim 47 wherein the electronics portion includes an electronic device for producing an audio output in the at least one speaker; the electronic device including a receiver associated with a wire-using or wireless transmitting or broadcasting device.

51. The article of claim 39 further including two speakers; one speaker being located at one ear portion and the other speaker being located at the other ear portion.

52. The article of claim 39 further including a receiver associated with a wireless electronic transmitting or broadcasting device.

53. The article of claim 39 further including at least one opening in the sleeve and a control portion extending through the opening.

54. The article of claim 39 further including at least one harness configured to secure any associated headphone, earphone, speaker, wires or other electronic device or its component inside the sleeve.

55. The article of claim 54 wherein the harness is elastic.

56. The article of claim 39 further including an opening for exposing an auxiliary jack for electronically connecting an electronic device to the at least one speaker.

57. The article of claim 39 further including a radio device connected to the at least one speaker.

58. The article of claim 39 further including an interchangeable or removable electronic device.

59. The article of claim 39 further including an opening configured for inserting and removing an electronic device.

60. The article of claim 39 further including an input jack for connecting the at least one speaker to an external electronic device.

61. An article for the ears comprising:
earmuffs having two insulating ear portions; each ear portion located at the ends of a band; and
at least one speaker located in at least one of the ear portions;
wherein at least one of the ear portions is a removable branding portion.

62. The article of claim 61 wherein at least one of the ear portions includes an opening adapted to expose a control portion to provide access to one or more control mechanisms.

63. The article of claim 61 wherein at least one of the ear portions includes an opening configured for inserting and removing an electronic device.

64. The article of claim 61 further including two speakers; one speaker being located at one ear portion and the other speaker being located at the other ear portion.

65. The article of claim 61 further including an electronic device for producing an audio output in the at least one speaker; the electronic device including a receiver associated with a wire-using or wireless transmitting or broadcasting device.

66. The article of claim 61 further including a receiver associated with a wireless electronic transmitting or broadcasting device.

67. The article of claim 61 further including at least one opening and a control portion extending through the opening.

68. The article of claim 61 further including a sleeve encompassing the earmuffs.

69. The article of claim 68 wherein an electronic wire is concealed within the sleeve.

70. The article of claim 68 further including an opening through which the at least one speaker can be inserted and removed.

71. The article of claim 61 further including a radio device connected to the at least one speaker.

72. The article of claim 61 further including an interchangeable or removable electronic device.

73. The article of claim 61 wherein an electronic wire is concealed within the band.

74. The article of claim 61 further including a first opening at the location of one of the ear portions.

75. The article of claim 74 further including a second opening at the location of the other ear portion.

76. The article of claim 61 further including an opening for exposing an auxiliary jack for electronically connecting an electronic device to the at least one speaker.

77. The article of claim 61 further including an input jack for connecting the at least one speaker to an external electronic device.

78. An article for the ears comprising:
earmuffs having two insulating ear portions; each ear portion located at the ends of a band;
at least one speaker located in at least one of the ear portions; and
means for interchangeable advertising.

79. The article of claim 78 wherein at least one of the ear portions includes an opening adapted to expose a control portion to provide access to one or more control mechanisms.

80. The article of claim 78 wherein at least one of the ear portions includes an opening configured for inserting and removing an electronic device.

81. The article of claim 78 further including two speakers; one speaker being located at one ear portion and the other speaker being located at the other ear portion.

82. The article of claim 78 further including an electronic device for producing an audio output in the at least one speaker; the electronic device including a receiver associated with a wire-using or wireless transmitting or broadcasting device.

83. The article of claim 78 further including a receiver associated with a wireless electronic transmitting or broadcasting device.

84. The article of claim 78 further including at least one opening and a control portion extending through the opening.

85. The article of claim 78 wherein said means for interchangeable advertising includes a branding portion having a branding location configured as a piece of material interchangeably mounted onto the branding portion.

86. The article of claim 78 wherein said means for interchangeable advertising includes a branding portion having a branding location configured as a cap having extension tabs configured to extend and snap into the branding portion to secure a branding or advertising piece onto the ear warming article.

87. The article of claim 78 wherein the means for interchangeable advertising includes an advertising patch.

88. The article of claim 87 wherein the advertising patch is connectable by a hook and loop type fastener, adhesive or tabs.

89. The article of claim 78 wherein the means for interchangeable advertising is permanently attached to a sleeve that encompasses the earmuffs; the sleeve being interchangeable.

90. The article of claim 78 wherein the means for interchangeable advertising is permanently attached.

91. The article of claim 78 wherein the means for interchangeable advertising includes a main branding zone.

92. The article of claim 91 wherein the main branding zone is located along the band.

93. The article of claim 78 wherein the means for interchangeable advertising includes a team logo.

94. The article of claim 78 further including a sleeve encompassing the earmuffs.

95. The article of claim 94 wherein an electronic wire is concealed within the sleeve.

96. The article of claim 94 further including an opening in the sleeve configured for inserting and removing an electronic device.

97. The article of claim 94 further including an opening located in the sleeve through which the at least one speaker can be inserted and removed.

98. The article of claim 94 comprising:
an electronics portion including the at least one speaker sandwiched between an exterior fabric portion and an interior fabric portion that together comprise the sleeve that encompasses the electronics portion, band and ear portions.

99. The article of claim 98 including at least one padding portion located between the interior fabric portion and the electronics portion.

100. The article of claim 78 further including a radio device connected to the at least one speaker.

101. The article of claim 78 wherein the means for interchangeable advertising is interchangeable by a user.

102. The article of claim 78 further including an interchangeable or removable electronic device.

103. The article of claim 78 wherein an electronic wire is concealed within the band.

104. The article of claim 78 further including at least one harness configured to secure any associated headphone, earphone, speaker, wires or other electronic device or its component inside the sleeve.

105. The article of claim 104 wherein the harness is elastic.

106. The article of claim 78 further including an opening for exposing an auxiliary jack for electronically connecting an electronic device to the at least one speaker.

107. The article of claim 78 further including an input jack for connecting the at least one speaker to an external electronic device.

* * * * *